(12) United States Patent
Kölbel et al.

(10) Patent No.: US 9,179,998 B2
(45) Date of Patent: Nov. 10, 2015

(54) DEVICE AND METHOD FOR TREATING VASCULAR DISSECTIONS

(71) Applicant: Cook Medical Technologies LLC, Bloomington, IN (US)

(72) Inventors: Tilo Kölbel, Hamburg (DE); Erik E. Rasmussen, Slagelse (DK)

(73) Assignee: Cook Medical Technologies LLC, Bloomington, IN (US)

( * ) Notice: Subject to any disclaimer, the term of this patent is extended or adjusted under 35 U.S.C. 154(b) by 200 days.

(21) Appl. No.: 13/832,738

(22) Filed: Mar. 15, 2013

(65) Prior Publication Data

US 2014/0277338 A1 Sep. 18, 2014

(30) Foreign Application Priority Data

Mar. 12, 2013 (GB) .................................. 1304428.4

(51) Int. Cl.
*A61F 2/06* (2013.01)
*A61F 2/07* (2013.01)
*A61F 2/958* (2013.01)

(52) U.S. Cl.
CPC . *A61F 2/07* (2013.01); *A61F 2/958* (2013.01); *A61F 2250/001* (2013.01); *A61F 2250/006* (2013.01); *A61F 2250/0039* (2013.01)

(58) Field of Classification Search
CPC ....... A61F 2/06; A61F 2/07; A61F 2250/001; A61F 2250/0039
USPC ................................ 623/1.11–1.16, 1.25, 1.3
See application file for complete search history.

(56) References Cited

U.S. PATENT DOCUMENTS

| | | | |
|---|---|---|---|
| 6,890,350 B1 * | 5/2005 | Walak | 623/1.15 |
| 8,002,816 B2 * | 8/2011 | Greenberg | 623/1.13 |
| 2004/0167605 A1 | 8/2004 | Elliott | |
| 2006/0100684 A1 * | 5/2006 | Elliott | 623/1.2 |
| 2007/0043425 A1 * | 2/2007 | Hartley et al. | 623/1.12 |
| 2009/0210048 A1 | 8/2009 | Amplatz et al. | |

(Continued)

FOREIGN PATENT DOCUMENTS

| | | |
|---|---|---|
| WO | 0236045 A2 | 5/2002 |
| WO | 2004049978 A1 | 6/2004 |

(Continued)

OTHER PUBLICATIONS

Application No. GB1304428.4 UK Combined Search and Examination Report Aug. 1, 2013.

(Continued)

*Primary Examiner* — Todd Manahan
*Assistant Examiner* — Erich Herbermann
(74) *Attorney, Agent, or Firm* — Richard J. Godlewski (57) ABSTRACT

An implantable medical device (30) for treating aortic dissections includes a stent graft part (34) having a bulbous section (48) of greater radial diameter than the radial diameter of first and second sections (60,62) of the stent graft part (34). The bulbous section (48) is able to close off the false lumen (10) of an aortic dissection, thereby to prevent any fluid backflow into the false lumen (10). Radiopaque markers (70) may be provided for orientation and deployment purposes. The device (30) is able to treat chronic dissections and reduce false lumen backflow, which remains otherwise an unresolved issue in the endovascular treatment of false lumen aneurysms.

20 Claims, 10 Drawing Sheets

(56) References Cited

U.S. PATENT DOCUMENTS

| | | |
|---|---|---|
| 2012/0239137 A1 | 9/2012 | Heuser et al. |
| 2012/0290067 A1* | 11/2012 | Cam et al. .................. 623/1.12 |
| 2014/0324154 A1* | 10/2014 | Shalev ...................... 623/1.13 |

FOREIGN PATENT DOCUMENTS

| | | |
|---|---|---|
| WO | 2008140796 A1 | 11/2008 |
| WO | 2011130579 A1 | 10/2011 |
| WO | 2012068298 A1 | 5/2012 |
| WO | 2013030818 A2 | 3/2013 |

OTHER PUBLICATIONS

European Search Report, Cook Medical Technologies LLC, Jun. 27, 2014.

* cited by examiner

DEVICE AND METHOD FOR TREATING VASCULAR DISSECTIONS

TECHNICAL FIELD

The present invention relates to a device, kit and method for the treatment of aortic disease and more particularly to the treatment of a form of aortic aneurysms known as aortic dissections.

BACKGROUND OF THE INVENTION

An aortic dissection is a form of aneurysm which often occurs in the descending aorta, in which the wall of the vessel tears to such an extent that blood under pressure passes between inner and outer layers of the torn wall to expand part of the wall into an inflated sac or path of blood, referred to as a false lumen. The false lumen so formed may extend some distance along the descending thoracic and abdominal aorta and open out into the aorta again further down from the tear.

It has been found that dissections may self-heal if the proximal entry tear is covered to prohibit blood flow and pressure connection between the true and the false lumen at the proximal part of the dissected aorta. Consecutively the inner, separated, layer of vessel wall is pressed against the outer layer and the vessel wall may remodel over time. This can usually be achieved by the use of a stent graft positioned in the true lumen covering the proximal entrance to the false lumen and by means of a stent graft disposed along the length of the inner layer. The stent acts to cover intimal tears, which are connections between the true and the false lumen. They also press the inner wall layer against the outer wall layer and secure patency of the true lumen. It has been found, however, the vessel wall can remodel, that is become unitary again more likely if the wall layers are pressed together shortly after having separated. Once the dissection has become chronic, that is, it has existed for any length of time, it becomes less likely to achieve remodelling of the vessel wall. In such a circumstance, the wall layers remain separate and the false lumen persists. Dissections may remain undetected in a patient for significant periods, in which case they may be treated before becoming chronic.

While there is a false lumen in the vessel there is the risk of blood backflow through the downstream opening into the false lumen. This backflow maintains pressure in the false lumen and in particular between the inner and outer vessel wall layers. Such backflow contributes to a failure to close off the false lumen, aneurysmal widening of the false lumen and eventual risk of rupture of the outer vessel wall.

An example of a known dissection device and method is disclosed, for instance, in WO-2011/0270377.

SUMMARY OF THE INVENTION

The present invention seeks to provide an improved device and method for treating vascular dissections.

According to an aspect of the present invention, there is provided an implantable medical device for treating a dissection, the device including:
a graft element provided with:
a first graft section of tubular form and having a first diameter;
an intermediate graft section of generally tubular form and having a second diameter greater than the first diameter;
a third graft section of tubular form and having a third diameter less than the second diameter, the intermediate graft section being disposed between the first and third graft sections; and
a first transition graft section between the first and intermediate graft sections, and a second transition section between the intermediate and third graft sections;
at least one first stent ring associated with the first graft section and having a first expanded operating diameter, at least one second stent ring associated with the intermediate graft section and having a second expanded operating diameter greater than said first expanded operating diameter, and at least one third stent ring associated with the third graft section;
the device having a first expanded diameter in which the first, intermediate and third graft sections have substantially the same expanded diameters, the device further having a second expanded diameter in which the intermediate graft section is expanded to said second diameter, being greater than the expanded diameters of the first and third graft sections.

The device taught herein provides one stented graft section of a greater diameter than the remainder of the graft and which in practice can span the widened diameter of a dissected vessel. A widening pressure can be applied at the location of the second graft section to rupture the inner vessel wall layer and then press the intermediate graft section against the outer wall layer. In so doing, the false lumen is closed off, preventing blood backflow into the false lumen. Thus, the false lumen can be effectively isolated even in cases where the dissection has become chronic.

The graft sections preferably form a generally complete occlusive barrier along the graft element. It is not excluded that the graft element may be provided with one or more fenestrations and/or branches.

Advantageously, the or each first and third stent ring is attached to its associated graft section. The or each second stent ring may also be attached to the intermediate graft section but in some embodiments the or each second stent ring is separate from the intermediate graft section.

Advantageously, the or each second stent ring is self-expandable. In other embodiments, the or each second stent ring is balloon expandable. A balloon expandable stent ring can generally be made stiffer and thus better able to press the false lumen closed.

The first and third stent rings are preferably self-expandable.

The intermediate graft section preferably provides a transversely extending bulbous section. The second graft section may include a side flush with, or aligned with, the first graft section and the or a third graft section. In other words, the intermediate graft section may extend in asymmetric fashion out of one side of the graft element.

Preferably, the transversely extending bulbous section and the transition graft section provide first and second tapers to the graft element. The intermediate graft section advantageously includes a side uniform with the first graft section and the or a third graft section.

In a practical embodiment, there is provided at least one radiopaque marker at the intermediate graft section, which may be attached to the graft element or attached to the or at least one second stent ring. The radiopaque markers are preferably disposed at the part of the intermediate graft section which extends beyond the diameter of the graft element, that is of the first and third graft sections.

In the preferred embodiment, the device includes an intermediate graft is element with associated stent rings, the intermediate graft element being generally tubular and sized to receive a portion of the first graft section therewithin.

Advantageously, the implantable medical device includes diameter reducing ties coupled to the graft sections. These enable the graft to be located in a patient's vessel and then oriented precisely with relation to a dissection prior to expansion of the graft element.

According to another aspect of the present invention, there is provided a kit including:

an implantable medical device, which device includes: a graft element provided with: a first graft section of tubular form and having a first diameter; an intermediate graft section of generally tubular form and having a second diameter greater than the first diameter; a third graft section of tubular form and having a third diameter less than the second diameter, the intermediate graft section being disposed between the first and third graft sections; and a first transition graft section between the first and intermediate graft sections, and a second transition section between the intermediate and third graft sections; and at least one first stent ring associated with the first graft section and having a first expanded operating diameter, at least one second stent ring associated with the second graft section and having a second expanded operating diameter greater than said first expanded operating diameter, and at least one third stent ring associated with the third graft section; and a balloon catheter including a deployment balloon, which deployment balloon has an inflated diameter at least as large as the second diameter.

Advantageously, the intermediate graft section has an intermediate graft section length and the deployment balloon has an inflated length no greater than the intermediate graft section length. Preferably, the deployment balloon has an inflated length substantially the same as the intermediate graft section length, although in some embodiments it may have a length smaller than the intermediate graft section length.

The kit may also include, in the case where the second stent rings are separate from the graft, one or more stent rings for implantation into the intermediate graft section. The second stent ring or rings may be prefitted to the deployment balloon.

In some embodiments, the kit may be provided with a plurality of second stent rings and deployment balloons of different operative or inflated diameters, such that a clinician can select the stent rings and balloon on the basis of the measured patient's vessel size and thereby to expand the intermediate graft section to said size.

According to another aspect of the present invention, there is provided a method of deploying an implantable medical device, which device includes:

a graft element provided with: a first graft section of tubular form and having a first diameter; an intermediate graft section of generally tubular form and having a second diameter greater than the first diameter; a third graft section of tubular form and having a third diameter less than the second diameter, the intermediate graft section being disposed between the first and third graft sections; and a first transition graft section between the first and intermediate graft sections, and a second transition section between the intermediate and third graft sections; and at least one first stent ring associated with the first graft section and having a first expanded operating diameter, at least one second stent ring associated with the intermediate graft section and having a second intermediate operating diameter greater than said first operating diameter, and at least one third stent ring associated with the third graft section;

the method including the steps of:

positioning the medical device in a radially contracted state in a patient's vessel;

radially expanding the graft element to a first expanded diameter in which the first, intermediate and third graft sections have substantially the same expanded diameters and press against the vessel walls;

deploying a balloon of a balloon catheter so as to radially expand the second stent rings to as to cause the intermediate graft section to press against the vessel wall and so as to cause the intermediate graft section to expand radially to a greater diameter than the expanded diameters of the first and third graft sections.

Advantageously, the device is deployed along a vessel dissection, thereby to treat a vascular dissection, for instance in the descending aorta.

Preferably, the intermediate graft section presses an inner wall layer of the vessel wall forming the dissection radially outwardly so as to rupture the inner wall layer at position of the intermediate graft section having the greater diameter.

The method advantageously includes the step of deploying the implantable medical device in a patient's vessel in a radially contracted configuration by means of diameter reducing ties, orienting the medical device in the patient's vessel and releasing the radial constriction to allow the medical device to expand against the vessel walls.

BRIEF DESCRIPTION OF THE DRAWING

Embodiments of the present invention are described below, by way of example only, with reference to the accompanying drawings, in which.

DESCRIPTION OF THE PREFERRED EMBODIMENTS

Throughout this specification the term proximal with respect to both human or animal vasculature will be used to refer to the region closest to the heart and similarly that part of the implantable medical device or prosthesis which when in use is closest to the heart; while the term distal will be used for regions of the human or animal vasculature further from the heart and similarly those parts of the implantable medical device or prosthesis which in use are further from the heart.

With regard to the deployment or introducer assembly, the term distal is also used to denote the part of the assembly which remains closest to the clinician during the medical procedure, and typically outside the patient, while the term proximal is also used to denote the end of the assembly which is furthest from the clinician and which is first fed endoluminally into the patient's vasculature, in practice to be closest to the heart.

The embodiments described below are in connection with a dissection in the descending aorta. It will be appreciated that the teachings herein are not limited to the treatment of aortic dissections or to dissections per se.

Figure 1:
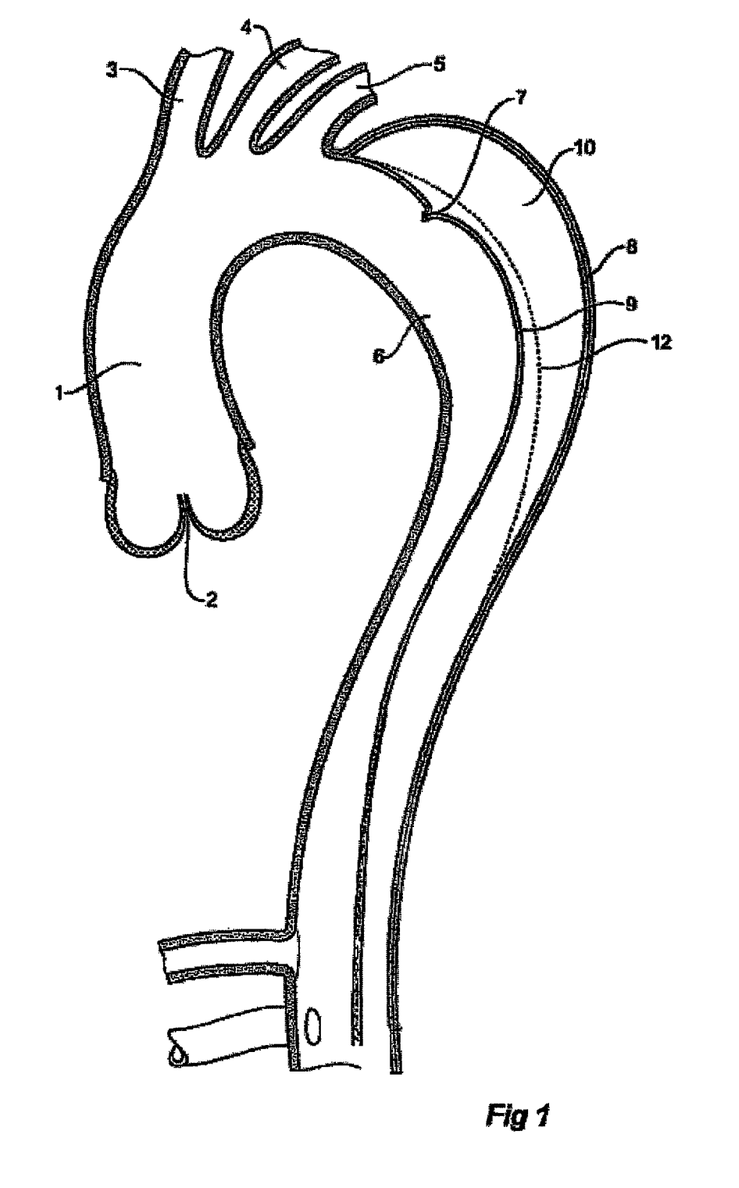
FIG. 1 shows a cross-sectional view of a patient's aorta having a dissection located in the descending aorta.

Referring to FIG. 1, it will be seen that the aorta comprises an ascending aorta 1 which receives blood from the heart though an aortic valve 2. At the upper end of the ascending aorta there are branches for the innominate artery 3 the left common carotid artery 4 and the subclavian artery 5. The aorta after these is referred to as the descending aorta 6 and it is in this region that an aortic dissection can occur. In an aortic dissection the wall of the descending aorta can be injured such as by a traumatic injury so that a partial rupture or tear 7 occurs and the wall of the descending aorta splits so that there is an outer wall 8 and an inner wall 9 between which a false lumen 10 is created. At some distance down the false lumen 10, the false lumen may again open out into the aorta 6 and the end of the dissection tear. The dotted line 12 shows the normal position of the wall of the aorta.

Treatment of the aortic dissection requires that the rupture 7 be closed off and the false lumen 10 deflated. While in many instances the placement of a stent graft along the dissection is sufficient to push the inner wall layer 9 against the outer wall layer 8 and thereby to close off the false lumen, it has been found that this can generally only be reliably achieved early in the life of the dissection. Once the dissection has become established, that is chronic, or where the inner wall layer 9 is too thick or strong or too long to be pushed back completely, the false lumen 10 cannot be properly closed off. An example of this situation can be seen in FIG. 2, where a stent graft 20 has been deployed in the descending aorta 6 along the dissection and in particular across the tear 7, thereby to close off the opening to the false lumen 10. The stent graft 20 may not extend along the entire length of the false lumen 10 when this is of substantial length, generally due to the existence of numerous side branches off the descending aorta. The false lumen 10 remains existent as a result of failure to press the entirety of the inner wall layer 9 and is liable to filling by fluid backflow 22. In this circumstance, the false lumen 10 does not collapse or close and the patient remains at risk of rupture of the outer wall 8 and thus of hemorrhaging.

False lumen backflow remains an unresolved issue in the endovascular treatment of false lumen aneurysms of the thoracic aorta, especially in the case of chronic dissections where the inner wall layer cannot readily be fully pressed against the outer wall layer.

Figure 3:
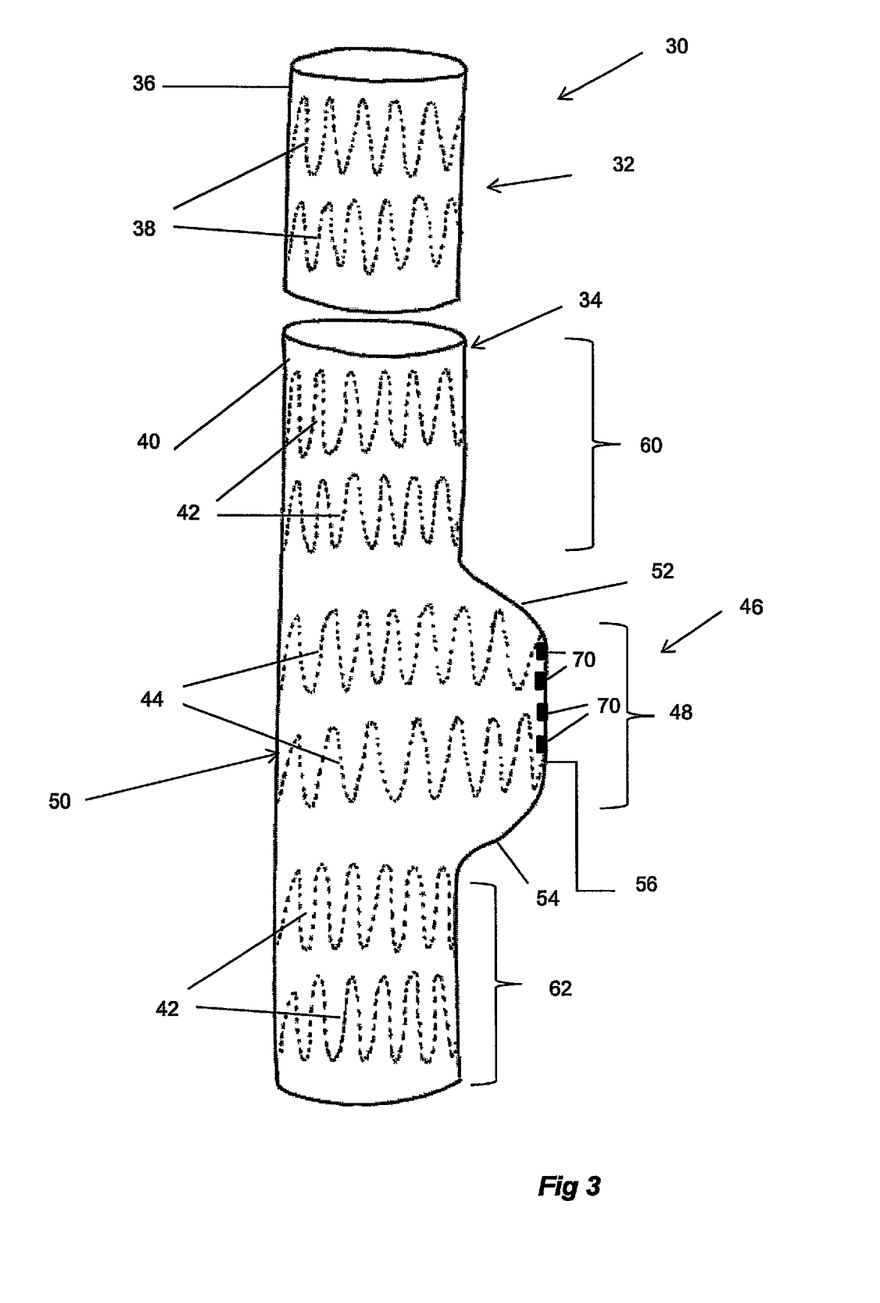
FIG. 3 is a schematic diagram of a preferred embodiment of implantable medical device as taught herein.

Referring now to FIG. 3, there is shown in schematic form a preferred embodiment of implantable medical device 30 suitable for treating dissections in the descending aorta. It will be appreciated, though, that the devices taught herein may be used for treating dissections in other vessels of a human or animal patient and may also be used for other medical indications, although are most appropriate for the treatment of dissections.

The device 30 in this embodiment includes first and second parts 32, 34, both being in the form of stent grafts. The first part 32 includes a tubular graft element 36 to which are attached a plurality of stent rings 38, which in this embodiment are of known zigzag form. The stents 38 are preferably made of a self-expanding material such as spring steel or polymer material and may also be made of shape memory material, including shape memory alloys such as Nitinol and shape memory polymers. The stent rings 38 may be fitted on the inside of or outside the graft tubing 36. The graft tubing 36 may be made of conventional graft material and is typically substantially fluid impervious. The tubing 36 is, in this example, of cylindrical form having a uniform diameter along its length. It is not excluded, though, that the tubing 36 could have a varying diameter along its length, in dependence upon the shape and configuration of the lumen into which the part 32 is to be located. The stent rings 38 have an operating diameter equivalent or similar to the diameter of the graft tubing 36.

Figure 2:
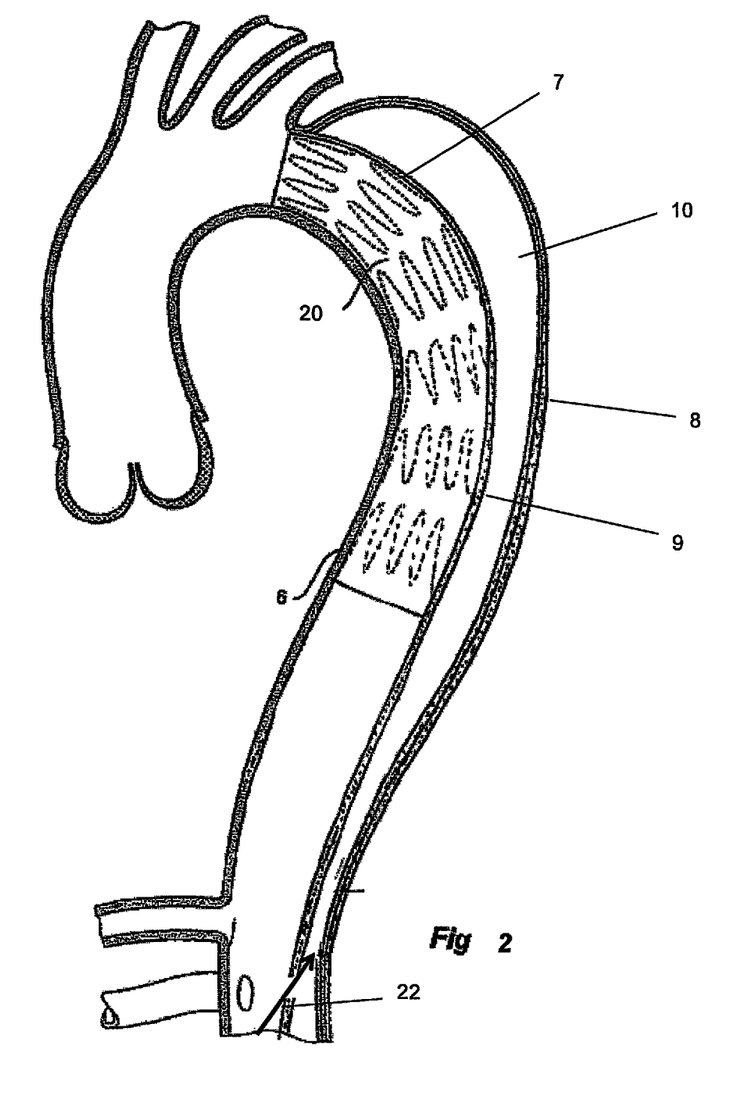
FIG. 2 is a schematic diagram of the aorta of FIG. 1 with a conventional stent graft deployed along the dissection.

It is to be understood that the first part 32 may be a conventional stent graft and could even be a stent graft as shown in FIG. 2. In such circumstances, the second part 34 described below, could be added to an existing dissection stent graft already fitted in a patient's vessel in the manner shown in FIG. 2. In some embodiments, though, the first part 32 is shorter than a stent graft traditionally used to treat a dissection. The second part 34, it will be appreciated, comprises the advantageous features taught herein.

The second part 34 of the device 30 also includes a graft element 40 and a plurality of stent rings 42 and 44. The graft element 40 is typically, but not necessarily, made of the same material as the graft element 36 of the first part 32. As can be seen in FIG. 3, the graft element 40 is generally cylindrical but has a radially enlarged section 46 which creates a bulbous region 48 to the part 34. The enlarged section 46 is referred to herein also as the intermediate graft section and the second graft section. It is preferred that the enlarged radial section 46 extends in one radial direction of the part 34 such that the majority of or a substantial part of the circumferential extent of the graft element, including the side 50, is substantially flush with the graft sections either side thereof. It is not excluded, though, that the enlarged section 46 may extend in a plurality of directions beyond the cylindrical perimeter of the remainder of the part 34.

The bulbous section 48 includes first and second tapering zones 52, 54 and a zone 56 which in this embodiment has a generally uniform diameter along its length.

The part 34 also includes a first or proximal graft section 60 which is generally cylindrical and in practice has a diameter substantially the same as the diameter of the first part 32 of the device 30. The part 34 also includes a third graft section 62 which is also generally cylindrical and preferably has a diameter the same or similar to the diameter of the first graft section 60. Thus, the first and third graft sections 60 and 62 have diameters less than the diameter of the second graft section 56. It is not excluded, though, that the section 34 may have a general taper along its length, for example to accommodate a varying lumen size, in which case the sections 60 and 62 may have slightly different diameters.

The graft part 34 is provided, in this embodiment, with two different sets of stent rings 42, 44. The first set of stent rings 42 are, in the preferred embodiment, similar to the stent rings 38 of the first part 32 of the device 30. They may, thus, be made of the same materials, although it is not excluded that they may be made of different materials. For example, the stent rings 38 of the section 32 may be self-expandable, whereas the stent rings 42 of the section 34 may be balloon expandable, or vice versa.

The stent rings 42 have an operating diameter which is the same as or substantially the same as the diameter of the graft tubing 40 at the locations at which the stent rings 42 are positioned.

On the other hand, the stent rings 44 of the second set of stent rings are larger than the stent rings 42, that is have a larger operating diameter and generally a diameter similar to or equivalent to the diameter of the second section 46 of the graft tubing 40. The stent rings 44 are thus able to apply an opening force to the second section 46 of the graft element 40 to attain the bulbous shape of that section.

In some embodiments the stent rings 44 may be made of the same material as the stent rings 42 and 38 but this is not essential. The stent rings 44 may, for example, be made of balloon expandable material, whereas the stent rings 42 may be made of a self-expanding material. A balloon expandable material can create stronger stent rings, useful in pressing a part of a dissection wall layer radially outwardly and potentially with greater force than that producible by a self-expanding stent ring. It is not excluded, though, that the stent rings 44 could be made of a self-expandable material.

As can be seen in FIG. 3, the device 30 is also provided with a plurality of radiopaque markers 70 at the bulbous section 48 and optionally also at the tapering portions 52, 54. The radiopaque markers, as will be apparent from the disclosure below, are useful in ensuring correct orientation of the part 34 in a patient's vessel and also in establishing correct deployment of the medical device 30 and expansion of the bulbous region 46.

Even though the embodiment of FIG. 3 shows a device 30 in two parts 32, 34, other embodiments provide a device of unitary form, that is with the upper or proximal part 32 integral with the lower or distal part 34.

Figure 4:
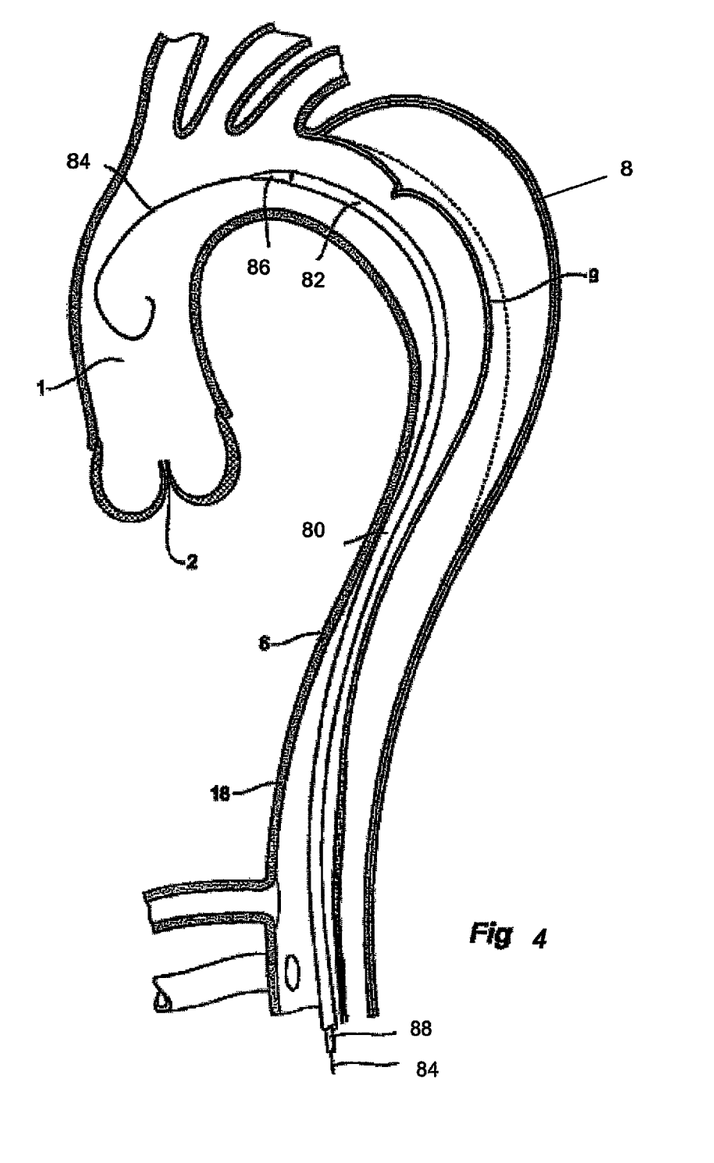
FIG. 4 is a schematic diagram of the proximal end of an embodiment of introducer assembly for deploying the device of FIG. 3.

Referring now to FIG. 4, there is shown an embodiment of introducer assembly 80 for the deployment of a device 30 as taught herein. The introducer assembly 80 includes an outer sheath 82 typically fed over a guide wire 84 in conventional manner and is provided also with a dilator tip 86 for assisting in the positioning of the sheath 82. The sheath 82 houses one or more carrier catheters 88 upon which are loaded the implantable medical device 30 as well as other components used in the deployment procedure, as described below. Typically, there can be provided a carrier catheter for each part of the medical device 30 and for deployment components such as balloon catheters, as is known in the art. The various elements of the assembly 80 will be apparent to the skilled person, particularly having regard to the description which follows.

FIG. 4 shows the first part 32 of the graft already fitted into the patient's lumen and positioned to close off the proximal dissection tear 7.

Figure 5:
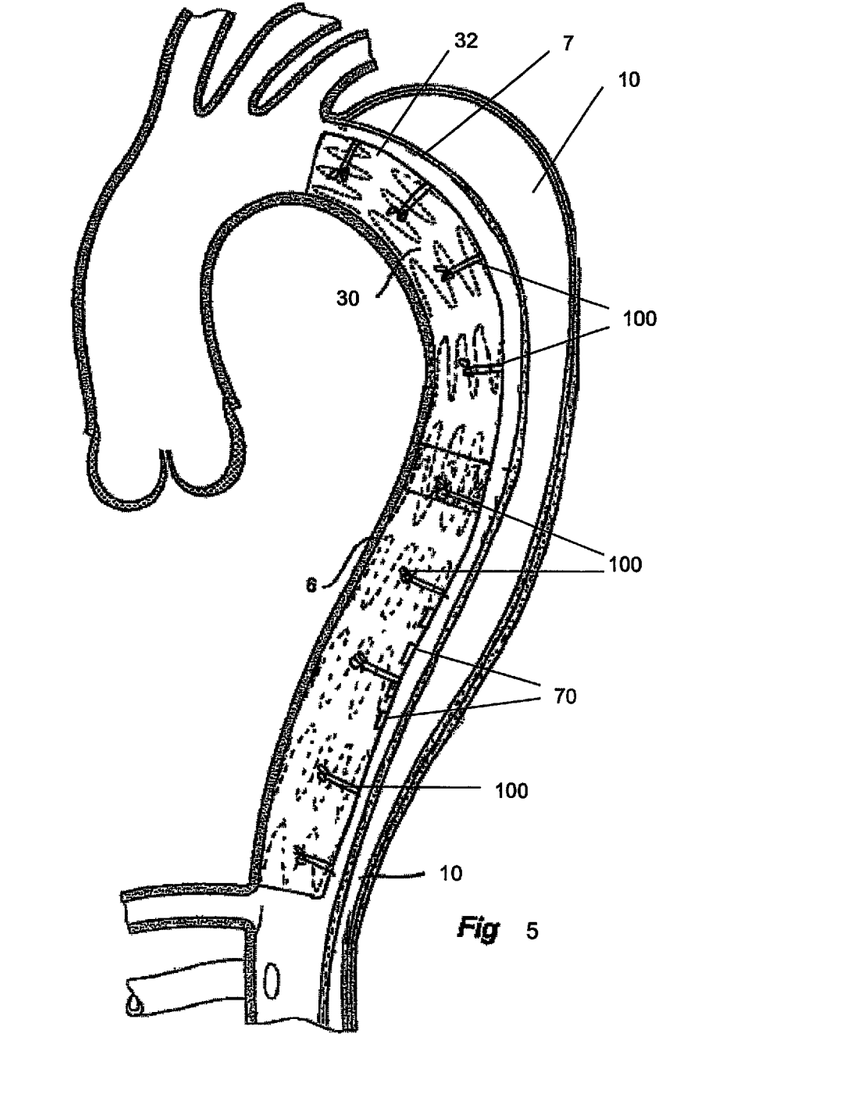
FIG. 5 is a schematic diagram showing the preferred embodiment of implantable medical device positioned in the descending aorta ready for final deployment.

Referring now to FIG. 5, there is shown in schematic form the implantable medical device 30 in a configuration in which it has been partially deployed in the descending aorta 6 of a patient's vessel. In this configuration, the medical device 30 has been positioned across the opening tear 7 to the false lumen 10 and along the false lumen, in the location it would reside in after full deployment.

The second part 34 of the medical device 30 includes a series of diameter reducing ties 100 which keep the stents 42, 44 in a contracted state, such that the second part 34 of the medical device 30 has a diameter in this configuration which is less than the diameter of the true lumen 6. In this state the second part 34 can be rotated in the aorta, using the radiopaque markers 70 to visualize its orientation. In this manner, the second part 34 can be accurately oriented in the vessel such that the bulbous section 48 faces the inner wall layer 9.

The skilled person will appreciate that in this configuration will still be held to the introducer assembly 80 to keep the diameter reducing ties 100 operative.

Figure 5A:
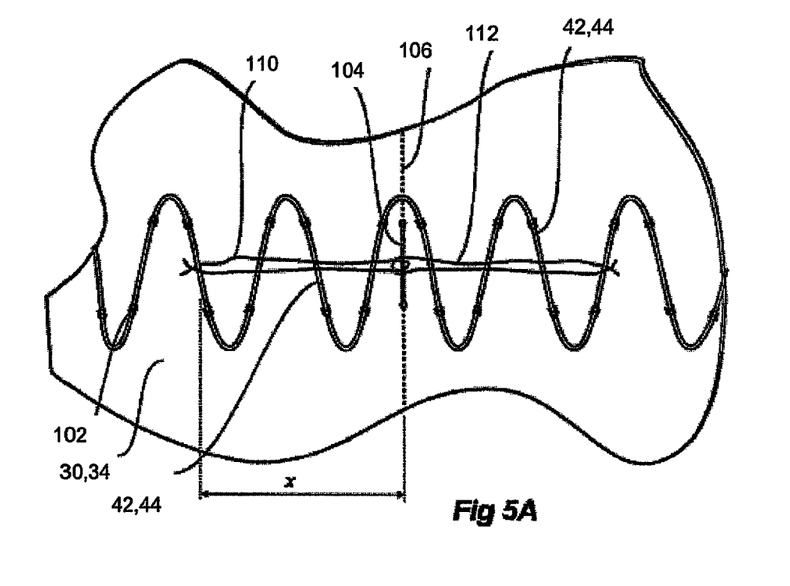
FIGS. 5A and 5B show a part of the implantable medical device of FIGS. 3 and 5 with diameter reducing ties provided thereon.
Figure 5B:
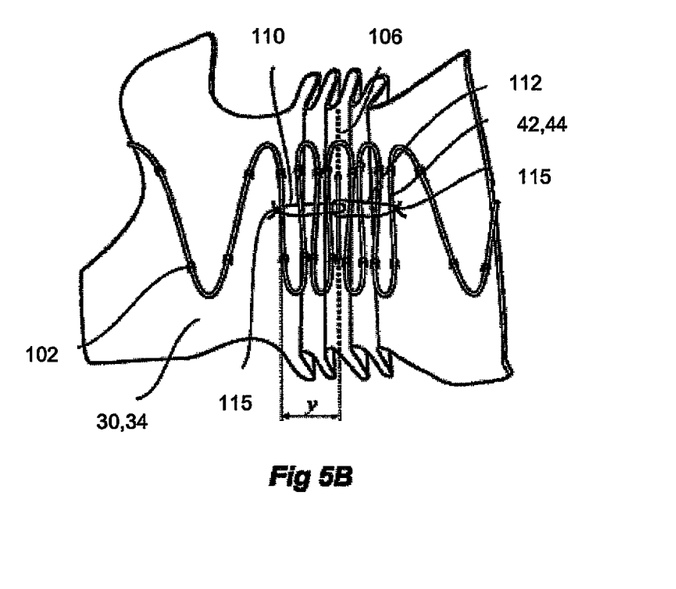

Referring now to FIGS. 5A and 5B, these show schematically one embodiment of diameter reducing tie arrangement. In this drawing only a portion of the graft material of a stent graft is shown and only a portion of a self-expanding stent is shown fastened to it and stretched out flat.

As can be seen in FIG. 5A, a stent 42, 44 which would extend around the tubular body 30, 34 of a stent graft and be stitched by stitches 102 to the graft material of the stent graft as shown. A release wire 104 is stitched longitudinally along the graft material of the stent graft a with a stitch 106 of the release wire being exposed to the outside of the stent graft in the region of the stent 42, 44.

A first suture thread 110 of a flexible material is passed around the release wire 104 and extends out to one side of the release wire over the struts of the stent 42, 44 to pass over two or three struts and to be looped around a third or fourth strut and into the graft material 42, 44. The suture thread 110 is then pulled tight and knotted as shown in FIG. 5B with a knot so that the struts between the release wire 104 and the knot are pulled closer together against the resilient force of the stent 42, 44. A similar action is carried out to the other side of the release wire with a second suture thread 112 of a flexible material. In this case the thread 110 can either pass around the release wire 104 or be passed underneath the two strands of the thread 110 and over the release wire 104 and then it can be passed over two or three struts and then looped around a third or fourth strut and into the graft material 42, 44 and pulled tight and knotted at 112.

The reduction in distance between the release wire 106 and the knot may be from 50 to 75 percent. For instance if the distance x in FIG. 5A is 15 millimeters around the circumference of the stent graft from the release wire 106 to the strut at which the knot is placed then this can be reduced to 5 millimeters as shown by the dimension y in FIG. 5B. With two diameter reducing ties, one to each side of the release wire 106, therefore a total circumference reduction of 20 millimeters can be achieved which will change the diameter of a 36 millimeter stent graft to approximately 28 millimeters. This can be less than the diameter of the aorta in that region into which the stent graft is deployed which means that the stent graft will still be manoeuvrable within the aorta while still mounted onto the deployment device but partially freed by the withdrawal of a containing sheath.

It is to be understood that diameter reducing ties may be located at different sides of the stent graft 34, with or without provision of the ties 100 shown in FIGS. 5 to 5B.

Figure 6:
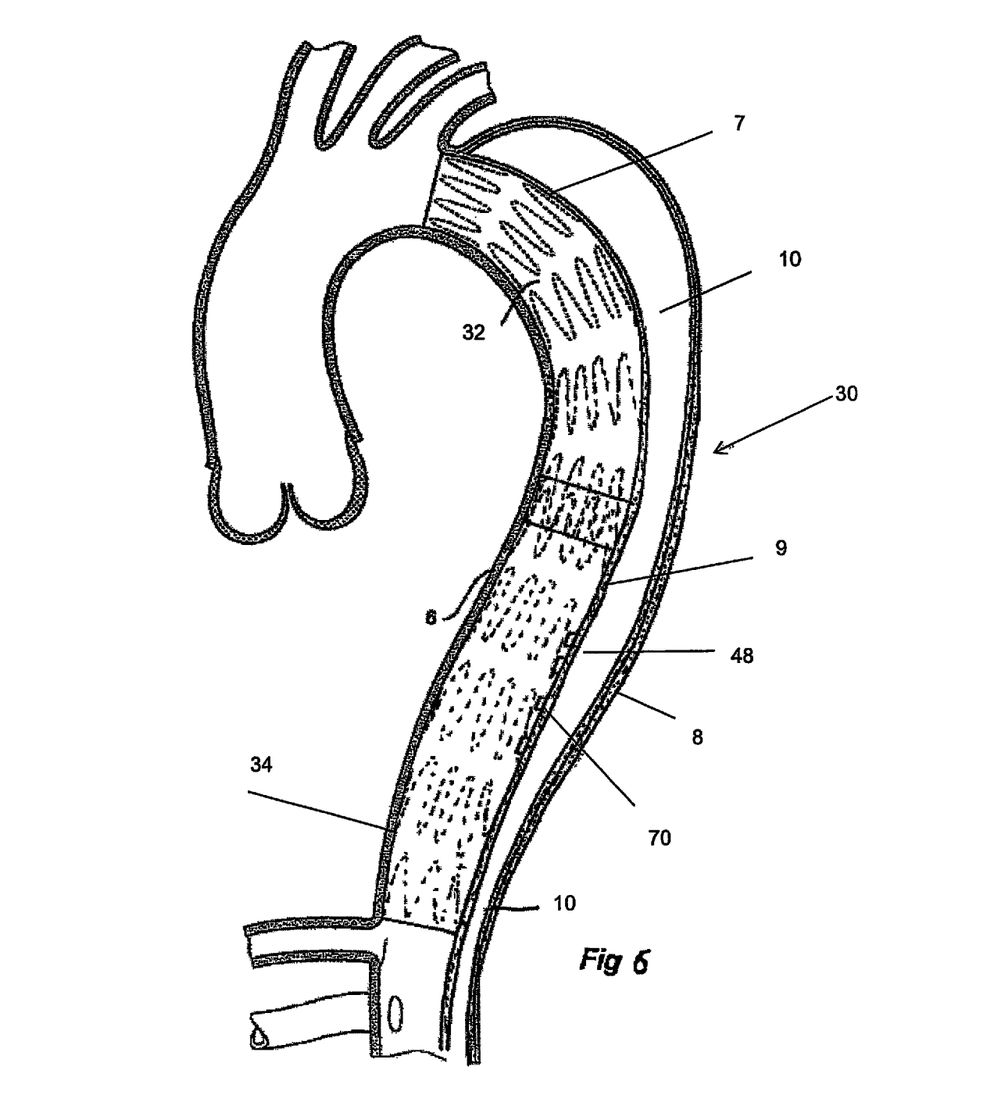
FIG. 6 is a view similar to FIG. 5 and showing implantable medical device radially expanded against the internal layer of the vessel wall.

Referring now to FIG. 6, there is shown in schematic form the implantable medical device 30 in a configuration in which it has been partially deployed in the descending aorta 6 of a patient's vessel, that is after it has been correctly oriented in the vessel and the release wire 106 (of FIG. 5) withdrawn to release the diameter reducing ties, thereby to allow the medical device 30 to expand to the vessel wall.

The first or proximal part 32 has been positioned in a proximal location so as to cover the rupture or tear 7 at the proximal end of the dissection, thus to close off the entrance into the false lumen 10. The second or distal section 34 has been positioned so as to overlap the first part 32, typically by having its proximal end expanded within the zone of the distal end of the part 32, and extends beyond the distal opening 11 into the false lumen 10, although it could terminate short of the distal opening 11. In this configuration, the bulbous section 48 has not yet been fully expanded and the second part 34 retains a generally cylindrical configuration throughout its length. The radiopaque markers 70 are useful in ensuring correct orientation of the second part 34, so as to ensure that the bulbous section 48 faces the inner vessel wall layer 9 of the dissection.

Figure 7:
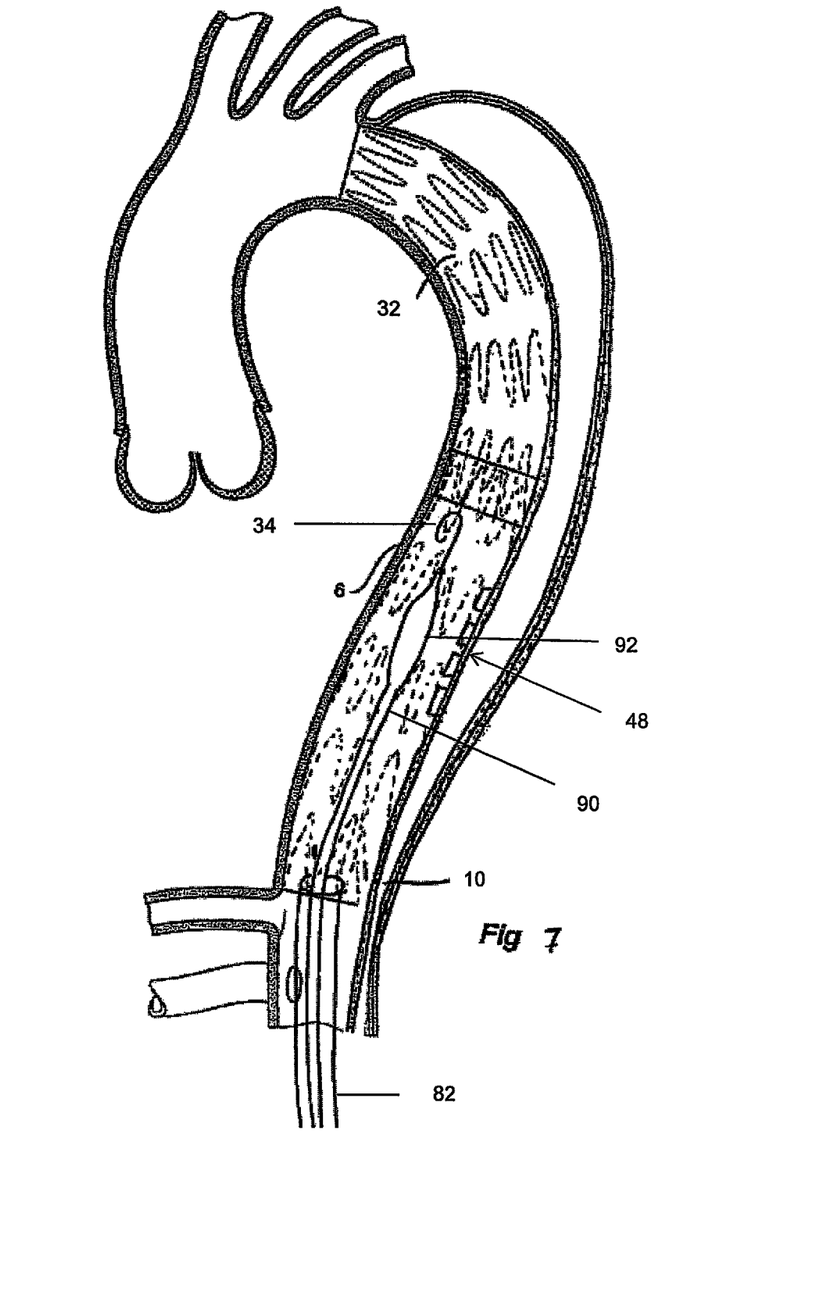
FIG. 7 is a view similar to FIGS. 5 and 6 and showing a balloon catheter of the deployment assembly positioned adjacent the second graft section.

Referring now to FIG. 7, through the sheath 82 there is fed a balloon catheter 90 to which there is fitted an inflatable balloon 92. The balloon 92 is positioned, in a deflated state, alongside the bulbous section 48. The balloon 92 preferably has a length which is the same as or substantially the same as the length of the bulbous section 48, although may be shorter than this or even somewhat longer.

Figure 8:
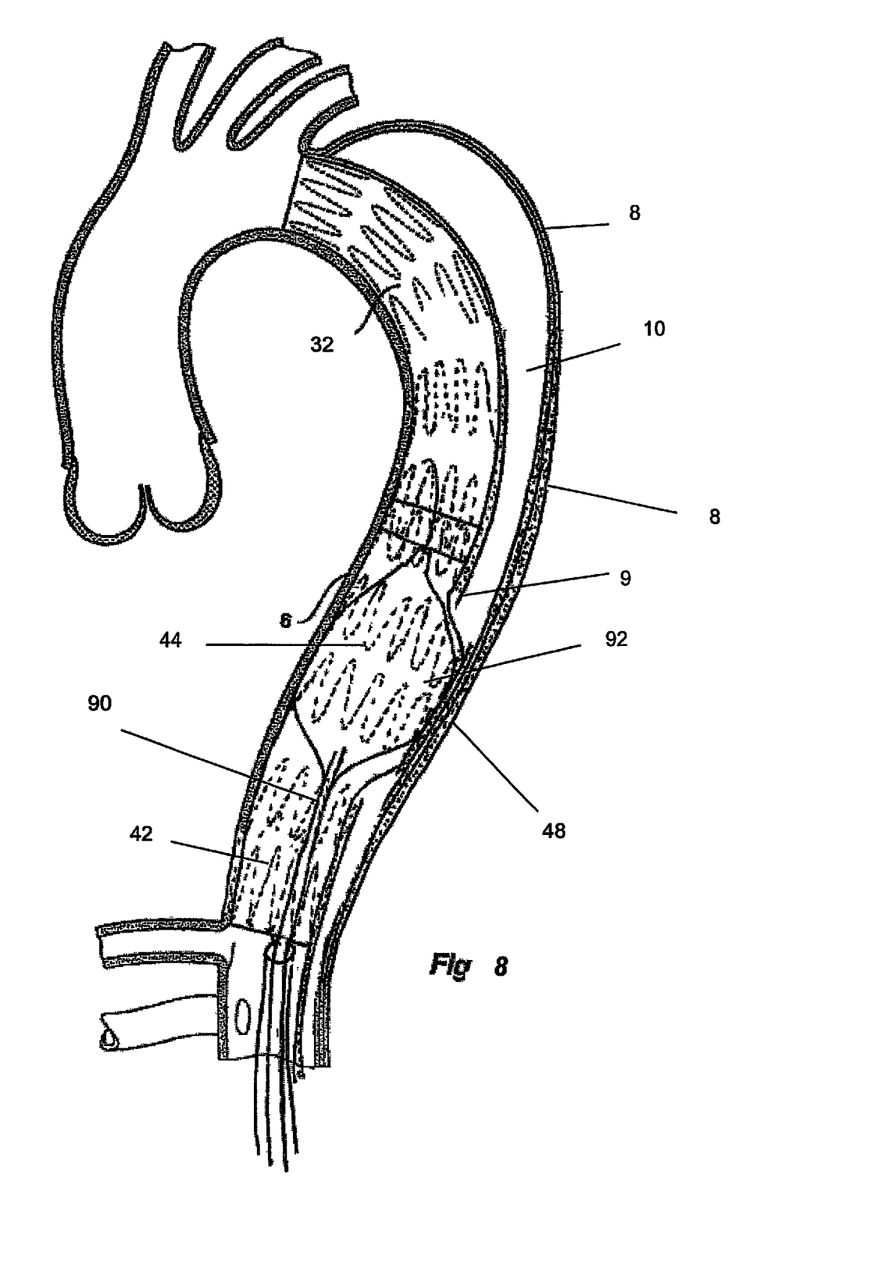
FIG. 8 is a view of the assembly of FIG. 7 with the balloon inflated so as to expand the second stent section and rupturing the inner wall layer.

Once positioned alongside the bulbous section 48, as can be seen in FIG. 8, the balloon 92 is inflated so as to cause radial expansion of the second graft section 48 and thus of the stent rings 44. The pressure produced by the balloon is sufficient to rupture the inner wall layer 9 and thereby to close off the false lumen 9 by expanding the bulbous portion 48 of the medical device 30 against the outer wall section 8.

Figure 9:
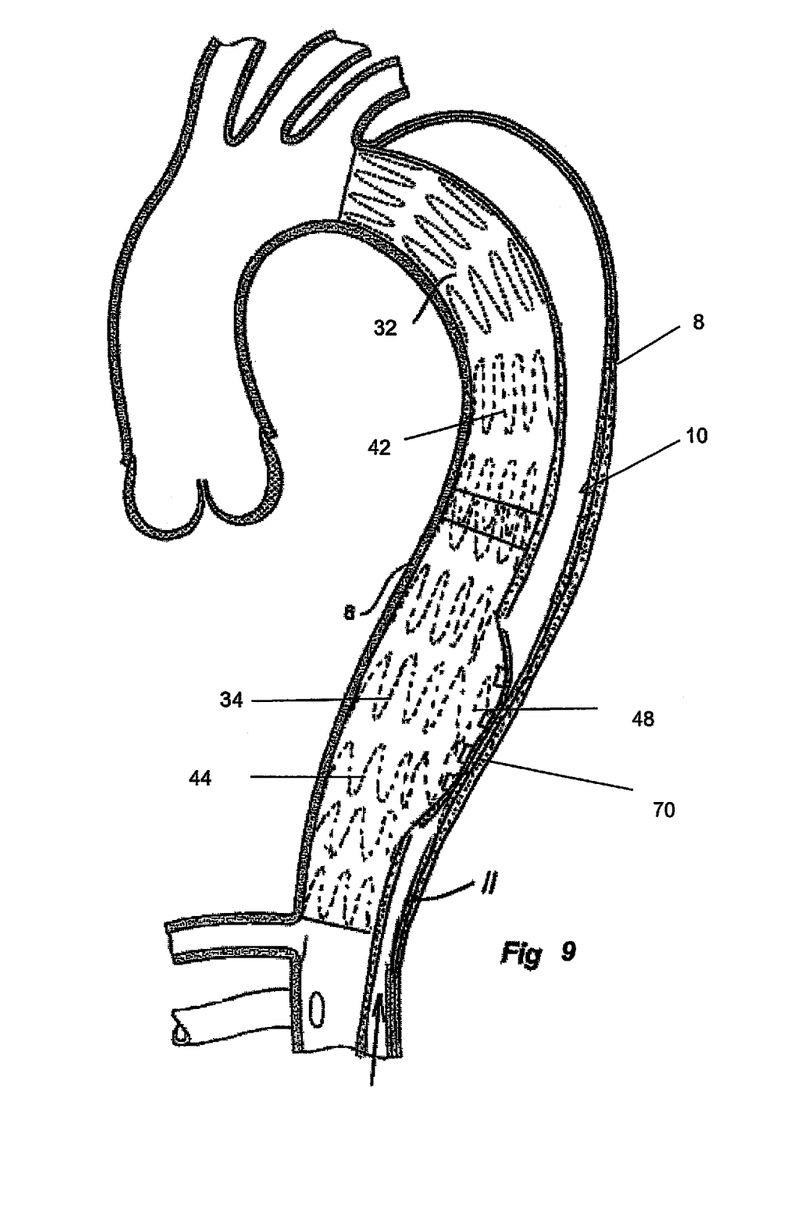
FIG. 9 shows the implantable medical device in a fully deployed configuration.

During its inflation, the balloon 92 will cause radial expansion of balloon expandable stent rings 44 but can also assist in the expansion of self-expanding stent rings 44 in the case where stent rings of the latter type are used. Once the false lumen has been closed in this manner, the stent rings 44 will act to retain the bulbous section 48 in its radially expanded configuration, as can be seen in FIG. 9, thereby to prevent any black flow into the false lumen. Once so closed, there will be no further blood pressure within the false lumen 10 and any blood therein will over time coagulate and as a result provide effective strengthening of the vessel at the location of the dissection. Closure of the false lumen to any fluid backflow will minimize the risk of rupture of the outer vessel wall layer 8 and even should such rupture occur blood loss will be limited to any blood located within the closed false lumen 10.

The eccentric bulbous section 48 does not provide a general radial expansion of the central or second part of the device 300 but directed expansion, so that it is predictable that the bulbous section 48 expands into the false lumen. When deployed, the first section 32 of the stent graft 30 is disposed in the true lumen, the second part 34 is disposed in both the true lumen and in the false lumen as the flap 9 is ruptured. The third section 62, again is located only in true lumen to direct the flow correctly.

It is to be understood that the second graft part 34 could be preloaded onto a balloon catheter 90 and thus deployed in a single step with the balloon catheter 90. This has the advantage of pre-aligning the balloon 92 with the bulbous section 48.

In another embodiment, however, the balloon catheter 90 is deployed in a secondary procedure as depicted in FIGS. 7 and 8. In this embodiment, it is envisaged that the stent rings 44 could be separate from the graft element 40, that is not pre-attached to the graft element 40. Such separate stent rings would be deployed after the positioning of the second part 34 in the vessel. In this regard, the stent rings 44 could be loaded onto the wrapped balloon 92 of the balloon catheter 90 and introduced into the patient with the balloon catheter 90. As the balloon 92 is inflated, the stent rings 44 will be radially expanded into the internal space of the second section 46 of the graft element 40, to expand this to create the bulbous region 48. The stent rings 44 will generally be held in position within the bulbous region 48 by virtue of their greater radial expansion compared to the remainder of the graft element 40. It is envisaged also that the stent rings 44 could be provided with barbs or other anchoring elements (not shown) which would assist in holding the stent rings 44 in place as well as the device part 34. Barbs of this type could be provided on some or all of the embodiments disclosed herein.

The provision of a section 48 of the implantable medical device 30 having a greater radial diameter enables only a part of the vessel wall layer 9 to be pushed radially outwardly, usually by rupturing this.

As will be apparent from the disclosure herein, the implantable medical device and deployment apparatus could be supplied in kit form. In this regard, the kit could provide a plurality of different sized second stent rings 44 and deployment balloons 92, able to expand the bulbous section 48 of the stent graft 40 to different diameters, in dependence upon the measured size of the vessel determined during the medical procedure. The kit may also include stent grafts 40 of different sizes.

It is to be understood that above are described various embodiments of the invention and that further modifications and embodiments will become apparent to a person skilled in the art, within the teachings herein. The described embodiments are intended to be illustrative and not limiting of the teachings herein.

What is claimed is:

1. An implantable medical device for treating a dissection, the device including:
   a graft element provided with:
      a first graft section of tubular form and having a first diameter;
      an intermediate graft section of cylindrical form having a length and a second diameter greater than the first diameter;
      a third graft section of tubular form and having a third diameter less than the second diameter, the intermediate graft section being disposed between the first and third graft sections; and
      a first transition graft section between the first and intermediate graft sections, and a second transition section between the intermediate and third graft sections;
   at least one first stent ring associated with the first graft section and having a first expanded operating diameter, at least one second stent ring associated with the intermediate graft section and having a second expanded operating diameter greater than said first expanded operating diameter, and at least one third stent ring associated with the third graft section; and
   the device having a first expanded diameter in which the first, intermediate and third graft sections have substantially the same expanded diameters, the device further having a second expanded diameter in which the intermediate graft section is expanded to said second expanded diameter wherein the second expanded diameter is cylindrical with a generally uniform diameter along the length of the intermediate graft section and greater than the expanded diameters of the first and third graft sections.

2. An implantable medical device according to claim 1, wherein the graft sections form a generally complete occlusive barrier along the graft element.

3. An implantable medical device according to claim 1, wherein each first and third stent ring is attached to the associated graft section.

4. An implantable medical device according to claim 1, wherein each first and third stent ring is self-expandable.

5. An implantable medical device according to claim 1, wherein each second stent ring is attached to the intermediate graft section.

6. An implantable medical device according to claim 1, wherein each second stent ring is separate from the intermediate graft section.

7. An implantable medical device according to claim 1, wherein each second stent ring is self-expandable.

8. An implantable medical device according to claim 1, wherein each second stent ring is balloon expandable.

9. An implantable medical device according to claim 1, wherein the intermediate graft section includes a transversally extending bulbous section.

10. An implantable medical device according to claim 9, wherein the transversally extending bulbous section and the transition graft sections provide at first and second tapers to the graft element.

11. An implantable medical device according to claim 1, wherein the intermediate graft section is asymmetrically disposed relative to the first and third graft sections.

12. An implantable medical device according to claim 1, wherein the intermediate graft section includes a side flush with the first and third graft sections.

13. An implantable medical device according to claim 1, including at least one radiopaque marker at the intermediate graft section.

14. An implantable medical device according to claim 13, wherein the at least one radiopaque marker is attached to the graft element.

15. An implantable medical device according to claim 14, wherein the at least one radiopaque marker is attached to the or at least one second stent ring.

16. An implantable medical device according to claim 1, wherein the device includes a second graft element with associated stent rings, the second graft element being generally tubular and sized to receive a portion of the first graft section therewithin.

17. An implantable medical device according to claim 1, including diameter reducing ties coupled to the graft sections.

18. An implantable medical device for treating a dissection, the device including: a graft element provided with: a first graft section of tubular form and having a first diameter; an intermediate graft section of generally cylindrical form having a length and a second diameter greater than the first diameter; a third graft section of tubular form and having a third diameter less than the second diameter, the intermediate graft section being disposed between the first and third graft sections; and a first transition graft section between the first and intermediate graft sections, and a second transition section between the intermediate and third graft sections; at least one first stent ring associated with the first graft section and having a first expanded operating diameter, at least one second stent ring associated with the intermediate graft section and having a second expanded operating diameter greater than said first expanded operating diameter, and at least one third stent ring associated with the third graft section; and the device having a first expanded diameter in which the first, intermediate and third graft sections have substantially the same expanded diameters, the device further having a second expanded diameter in which the intermediate graft section is expanded to said second expanded diameter wherein the second expanded diameter is cylindrical with a generally uniform diameter along the length of the intermediate graft section and greater than the expanded diameters of the first and third graft sections and the intermediate graft section at the second expanded diameter is asymmetrically disposed relative to the first and third graft sections.

19. A method of deploying an implantable medical device, which device includes: a graft element provided with: a first graft section of tubular form and having a first diameter; an intermediate graft section of cylindrical form having a second diameter greater than the first diameter; a third graft section of tubular form and having a third diameter less than the second diameter, the intermediate graft section being disposed between the first and third graft sections; and a first transition graft section between the first and intermediate graft sections, and a second transition section between the intermediate and third graft sections; the intermediate graft section having a generally uniform diameter along its length; and at least one first stent ring associated with the first graft section and having a first expanded operating diameter, at least one second stent ring associated with the intermediate graft section and having a second intermediate operating diameter greater than said first operating diameter, and at least one third stent ring associated with the third graft section; the method including the steps of: positioning the medical device in a radially contracted state in a patient's vessel; radially expanding the graft element to a first expanded diameter in which the first, intermediate and third graft sections have substantially the same expanded diameters and press against the vessel walls; and deploying a balloon of a balloon catheter so as to radially expand the at least one second stent ring so as to cause the intermediate graft section to form an cylindrical asymmetric section with a generally uniform diameter along the length of the intermediate graft section and so as to press the asymmetric section against the vessel wall and so as to cause the intermediate graft section to expand radially to a greater diameter than the expanded diameters of the first and third graft sections.

20. A kit including: an implantable medical device, which device includes: a graft element provided with: a first graft section of tubular form and having a first diameter; an intermediate graft section of cylindrical form and having a second diameter greater than the first diameter; a third graft section of tubular form and having a third diameter less than the second diameter, the intermediate graft section being disposed between the first and third graft sections and having a length; and a first transition graft section between the first and intermediate graft sections, and a second transition section between the intermediate and third graft sections; and at least one first stent ring associated with the first graft section and having a first expanded operating diameter, at least one second stent ring associated with the intermediate graft section and having a second expanded operating diameter greater than said first expanded operating diameter, wherein the second expanded diameter is cylindrical with a generally uniform diameter along the length of the intermediate graft section and at least one third stent ring associated with the third graft section; and a balloon catheter including a deployment balloon, which deployment balloon has an inflated diameter at least as large as the second diameter.

\* \* \* \* \*